(12) United States Patent
Stuart

(10) Patent No.: US 7,140,379 B2
(45) Date of Patent: Nov. 28, 2006

(54) CROSS-OVER PREVENTION VALVE

(75) Inventor: Graham M. Stuart, Redhill (GB)

(73) Assignee: Risbridger Limited, Surrey (GB)

( * ) Notice: Subject to any disclaimer, the term of this patent is extended or adjusted under 35 U.S.C. 154(b) by 341 days.

(21) Appl. No.: 10/685,303

(22) Filed: Oct. 14, 2003

(65) Prior Publication Data

US 2004/0112428 A1    Jun. 17, 2004

(30) Foreign Application Priority Data

Oct. 16, 2002    (GB) .................................. 0224110.7

(51) Int. Cl.
*F16K 17/40*    (2006.01)
(52) U.S. Cl. .................. 137/68.11; 251/66; 251/305
(58) Field of Classification Search ................. 137/67, 137/68.11; 251/66, 305, 308
See application file for complete search history.

(56) References Cited

U.S. PATENT DOCUMENTS

| 3,472,253 | A | * | 10/1969 | Bartz et al. ................ 137/67 |
| 3,586,018 | A | * | 6/1971 | Bogardh et al. ............... 137/67 |
| 3,846,795 | A | * | 11/1974 | Jones ........................ 340/540 |
| 4,271,120 | A | * | 6/1981 | Michaud ...................... 422/53 |
| 5,036,875 | A | * | 8/1991 | Thiltgen ..................... 137/74 |
| 5,960,811 | A | * | 10/1999 | Partridge ................ 137/68.11 |
| 6,644,336 | B1 | * | 11/2003 | Dolan ..................... 137/68.11 |

FOREIGN PATENT DOCUMENTS

WO    WO 00/55598    *    9/2000

* cited by examiner

*Primary Examiner*—Ramesh Krishnamurthy
(74) *Attorney, Agent, or Firm*—Andrus, Sceales, Starke & Sawall, LLP

(57) ABSTRACT

A valve mechanism which is resiliently biassed towards a first position but is normally retained in a second position by means of a linkage including a chemically sensitive device which is arranged to release in the presence of a contaminant.

2 Claims, 3 Drawing Sheets

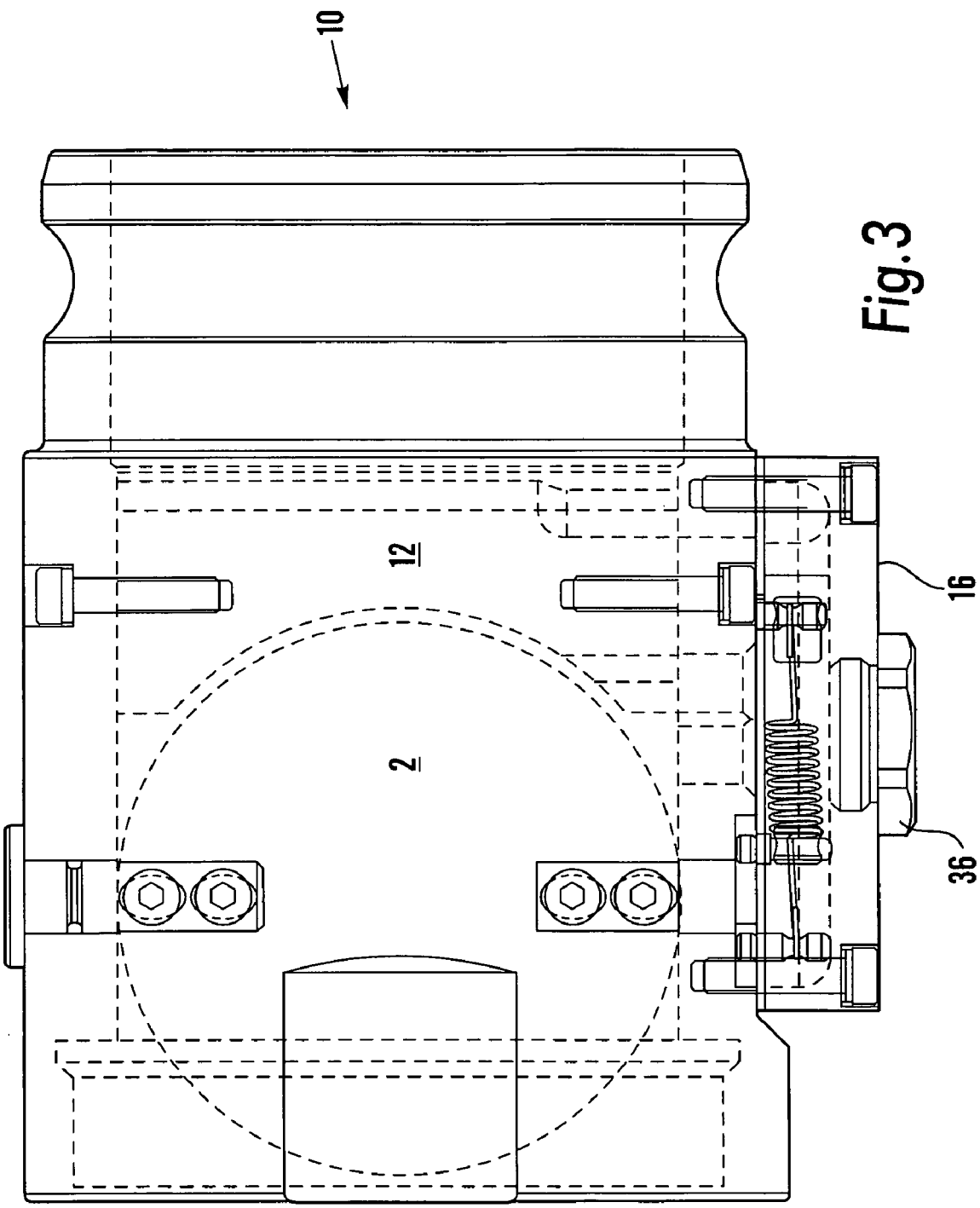

CROSS-OVER PREVENTION VALVE

FIELD OF THE INVENTION

This invention relates to a valve intended for installation at the inlet of a fluid tank, and in particular, to a valve which is intended to prevent the contents of the tank from becoming contaminated, as a result of being filled with the wrong fluid.

BACKGROUND OF THE INVENTION

In large multiple fuel tank installations, for example on petrol station forecourts, there may be a number of storage tanks intended for different grades or types of fuel. Unintentional contamination of one fuel by another, can easily take place if care is not taken when the fuels are delivered and, can cause considerable damage, for example if diesel fuel finds its way into a petrol tank, or vice versa. Since all of these fuels are commonly delivered by tankers with multiple fuel compartments, and all of the storage tanks have similar filler inlets, such an error can easily occur if the tanker operative is in a hurry.

International patent application no. WO 00/55598 (Masstech International Limited) describes a device for detecting the presence of a chemical contaminant, the device comprising an indicator element which is held in a first position by means of a failure element which is held in tension, the failure element being made of a material which fails in the presence of the chemical to be detected, thereby releasing the indicator element from its first position and allowing it to move into a second position in order to provide an indication of the presence of the contaminant.

The failure of the failure element may occur by shearing or stretching of the element, or, more typically, may occur when the surface of the element is degraded by the contaminant, in such a way as to release it from engagement with another part of the mechanism.

SUMMARY OF THE INVENTION

The present invention utilises a similar arrangement, in order to trigger the movement of a valve member, in the presence of a contaminant. Accordingly, the present invention provides a valve mechanism which is resiliently biassed towards a first position but is normally retained in a second position by means of a linkage including a chemically sensitive device which is arranged to release in the presence of a contaminant.

Preferable the valve is biassed towards a closed position but is normally held open by the retaining linkage.

Preferably, the chemically sensitive device comprises an elongate tie member, at least one end of which is frictionally engaged by a cooperating member which connects it to the remainder of the valve mechanism, and whose surface is chemically degraded by the contaminant so that the frictional engagement is lost. For example, the failure element may be made from a material which is dissolved by the contaminant, or may have a surface whose co-efficient of friction changes in the presence of the contaminant. This may result from a change in viscosity of the surface.

In a preferred embodiment, the valve mechanism includes a movable closure element mounted in a conduit, which is resiliently biassed towards a position in which it closes the conduit, but is held in the open position, against the resilient bias, by means of a chemically sensitive device of the type described above.

BRIEF DESCRIPTION OF THE DRAWING

One embodiment of the invention will now be described, by way of example, with reference to the accompanying drawings in which:

FIG. 3 is a plan view of the device of FIG. 1, again showing some hidden detail.

DETAILED DESCRIPTION

Figure 1:
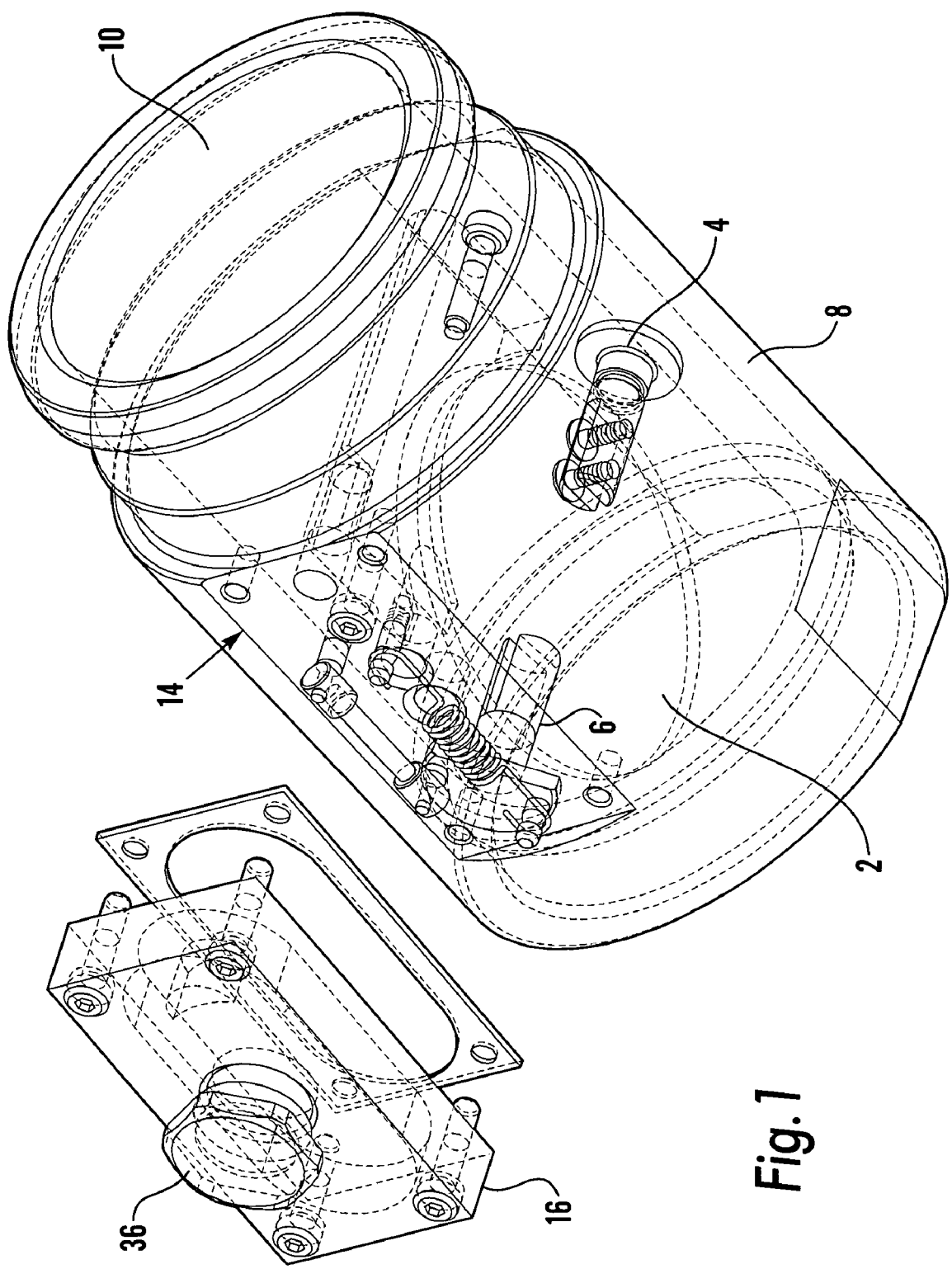
FIG. 1 is a perspective view of a device according to the invention, showing some hidden detail.

Referring to FIG. 1, the device as illustrated includes a circular butterfly valve member 2 pivotally mounted on trunnions 4 and 6 in a conduit 8. As shown, the valve is in the open position in which the butterfly is parallel to the axis of the conduit, and is shielded from flow turbulence forces at the inlet 10, by a transversely extending fixed vane plate member 12 which also provides an Intake port for housing 60.

Figure 2:
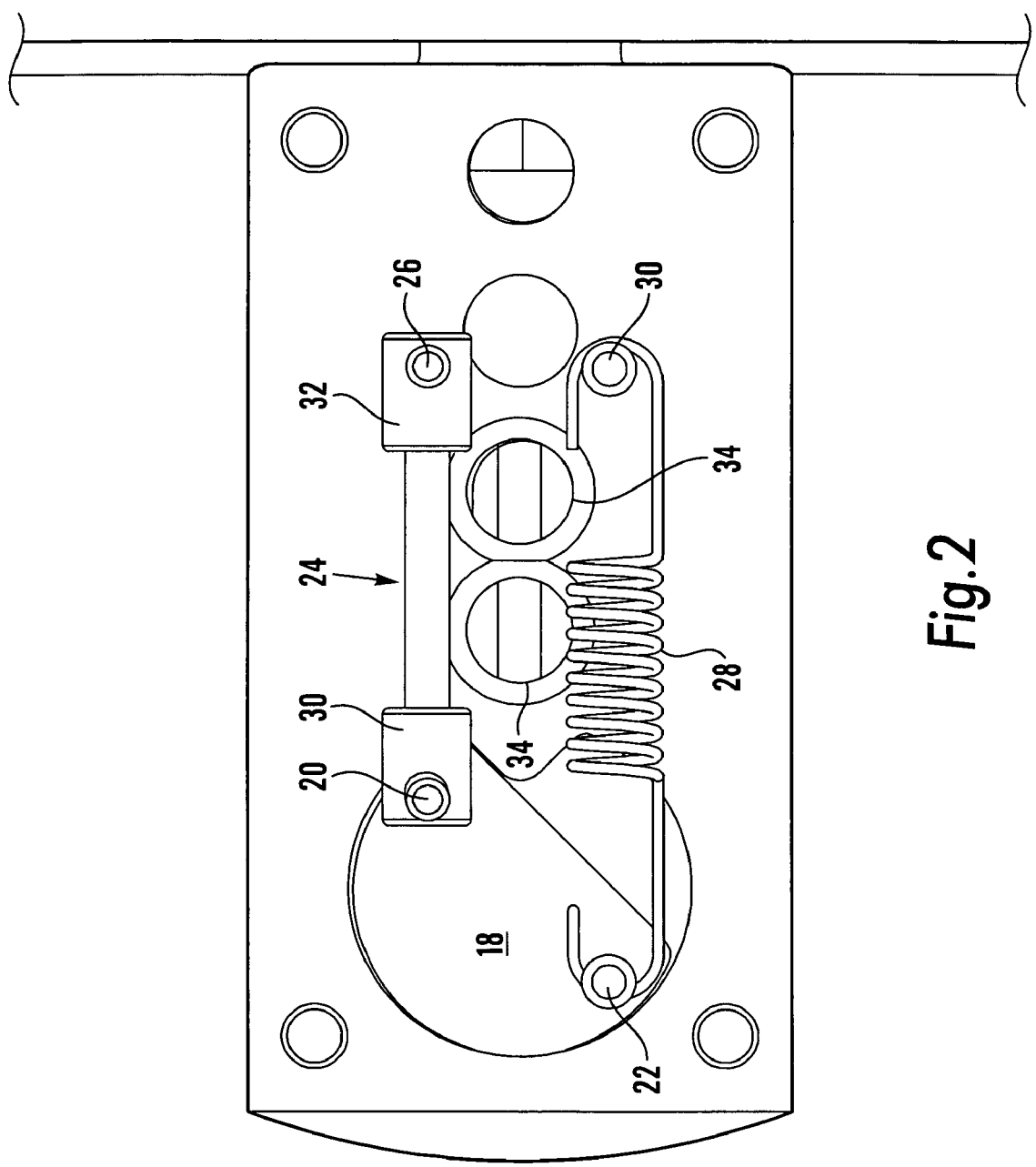
FIG. 2 is an enlarged side elevation of part of the device of FIG. 1

The trunnion member 6 is connected to an actuating mechanism 14 mounted on the outside of the conduit 8, in a housing 16. As shown in more detail in the enlarged view of FIG. 2, the mechanism comprises a plate member 18 forming a crank arm, and having axially extending pins 20 and 22 mounted at opposite ends of a diameter of the plate which, in the open position shown, is at 45° to the axis of the conduit.

The upper pin 20 is connected by means of a chemically sensitive device comprising a "chemical fuse" 24, described in more detail below, to a fixed pin 26 of the mechanism, whilst the lower pin member 22 is connected by a tension spring 28 to a further fixed pin member 30.

In the example illustrated, the "chemical fuse" member 24 comprises a tubular member of material which is chemically sensitised to a contaminant, in such a way that its surface characteristics change rapidly in the presence of the contaminant. The tubular member is provided with end caps 30 and 32 having axial bores which are a close interference fit on the ends of the tube, and transverse bores to receive the locating pins 20 and 26.

In operation, if a contaminant fluid enters the conduit, a sample portion of fluid will enter the housing 16 via intake aperture 35, and will exit housing 16 via apertures 34, into the low pressure zone downstream of vane member 12. This through flow fluid will contact and react with the surface of the "chemical fuse" member, so that the outer surface will rapidly degrade. Under these conditions end caps 31, 32 become a slightly looser fit, until the tension spring 28 overcomes the retaining force of the fuse member. At this point the spring will deflect the butterfly member 2 into the main flow stream. Flow forces will then assist the spring to rapidly close the butterfly valve over the full 90° movement.

As illustrated, the housing 16 of the valve member is provided with drain plug 36 so that in the event of a shut-off condition contamination fluid upstream of the closed butterfly member 2 can be drained away externally. This plug can also be used to take fluid samples.

In addition, the entire housing can be dismantled, to replace the "chemical fuse" when it has been triggered.

It will be appreciated that as illustrated, the device is arranged to close a filler Inlet in the event of detection of a predetermined substance. However, it could equally be employed in a context where it was required to open in the presence of a predetermined substance, for example to allow it to escape through an overflow.

The invention claim is:

1. A valve mechanism including a movable closure member, means for resiliently biasing the movable member towards a first position, and linkage means for retaining the movable member in a second position, the linkage means including a chemically sensitive fuse which is arranged to release in the presence of a contaminant, the first position and second position being respective closed and open positions or respective open and closed positions, the movable closure member being a butterfly which is rotatably mounted in a conduit so as to close the conduit when the chemically sensitive fuse is activated, the chemically sensitive fuse being an elongate member having end caps which are an interference fit on each end, one of the end caps being connected to a crank arm so that the end cap is released when the surface of the chemically sensitive fuse is degraded by the contaminant.

2. A valve mechanism according to claim 1 in which the crank arm is connected to the rotatable butterfly, and a tension spring connects the crank arm to a fixed point so as to bias it to the closed position, the chemically sensitive fuse being arranged to retain the crank arm in the open position.

* * * * *